US00PP29291P2

(12) United States Plant Patent
Dirr et al.

(10) Patent No.: US PP29,291 P2
(45) Date of Patent: May 15, 2018

(54) ***LOROPETALUM* PLANT NAMED 'PIILC-IV'**

(50) Latin Name: ***Loropetalum chinense* var. *rubrum***
Varietal Denomination: PIILC-IV

(71) Applicant: Bailey Nurseries Inc, Newport, MN (US)

(72) Inventors: Michael A. Dirr, Bogart, GA (US); Rhonda Helvick, Madison, GA (US); Oren McBee, Bishop, GA (US); Mark Griffith, Watkinsville, GA (US); Jeff Beasley, Lavonia, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days. days.

(21) Appl. No.: 15/530,606

(22) Filed: Feb. 6, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new and distinctive cultivar of *Loropetalum* named 'PIILC-IV' that is characterized by its compact, mounded, spreading growth habit, its foliage that is dark purple in color that changes to green in color summer through winter, its flowers that are red-purple in color, and its good cold hardiness with hardiness at least in U.S.D.A. Zones 7 to 9.

2 Drawing Sheets

Botanical classification: *Loropetalum chinense* var. *rubrum.*

Variety denomination: 'PIILC-IV'.

BACKGROUND OF THE INVENTION

The present invention relates to a new and distinct cultivar of *Loropetalum chinense* var. *rubrum* and will be referred to hereafter by its cultivar name, 'PIILC-IV'. 'PIILC-IV' is an evergreen shrub grown for use as an ornamental landscape plant.

'PIILC-IV' originated as a seedling from seed derived from open pollination of *Loropetalum chinense* var. *rubrum* 'GriffCRL' (U.S. Plant Pat. No. 16,615). The male parentage is therefore unknown. The Inventor selected 'PIILC-IV' as a single unique plant in the summer of 2012 from amongst the resulting seedlings.

Asexual propagation of the new cultivar was first accomplished by one of the Inventors using semi-hardwood cuttings in Watkinsville, Ga. in 2013. Asexual propagation by semi-hardwood cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'PIILC-IV' as a unique cultivar of *Loropetalum.*

1. 'PIILC-IV' exhibits a compact, mounded, spreading growth habit.
2. 'PIILC-IV' exhibits foliage that is dark purple in color that changes to green in color summer through winter.
3. 'PIILC-IV' exhibits flowers that are red-purple in color.
4. 'PIILC-IV' exhibits good cold hardiness and is cold hardy at least in U.S.D.A. Zones 7 to 9.

The female parent of 'GriffCRL', 'PIILC-IV', differs from 'PIILC-IV' in having a rounded plant habit, a multi-stem trunk, a taller mature height of over 3.6 m, flowers that are vibrant fuchsia in color, immature and mature foliage that is grey-purple in color. 'PIILC-IV' can also be compared to *Loropetalum chinense* var. *rubrum* cultivars 'PIILC-IV' (U.S. Plant Pat. No. 25,470) and 'PIILC-III' (U.S. Plant Pat. No. 25,471). 'PIILC-II' differs from 'PIILC-IV' in having foliage that is ruby red in color maturing to purplish green, and flowers that are red-pink in color. 'PIILC-III' differs from 'PIILC-IV' in having foliage that is dark purple in color persistently year around, and flowers that are dark pink in color.

BRIEF DESCRIPTION OF THE DRAWINGS

The accompanying colored photographs illustrate the overall appearance and distinct characteristics of the new *Lorepetalum*. The photographs were taken of a four year-old plant of 'PIIIP-I' as grown in the ground in Watkinsville, Ga.

The photograph in FIG. 1 provides a side-view of the plant habit of in bloom.

Figure 1:
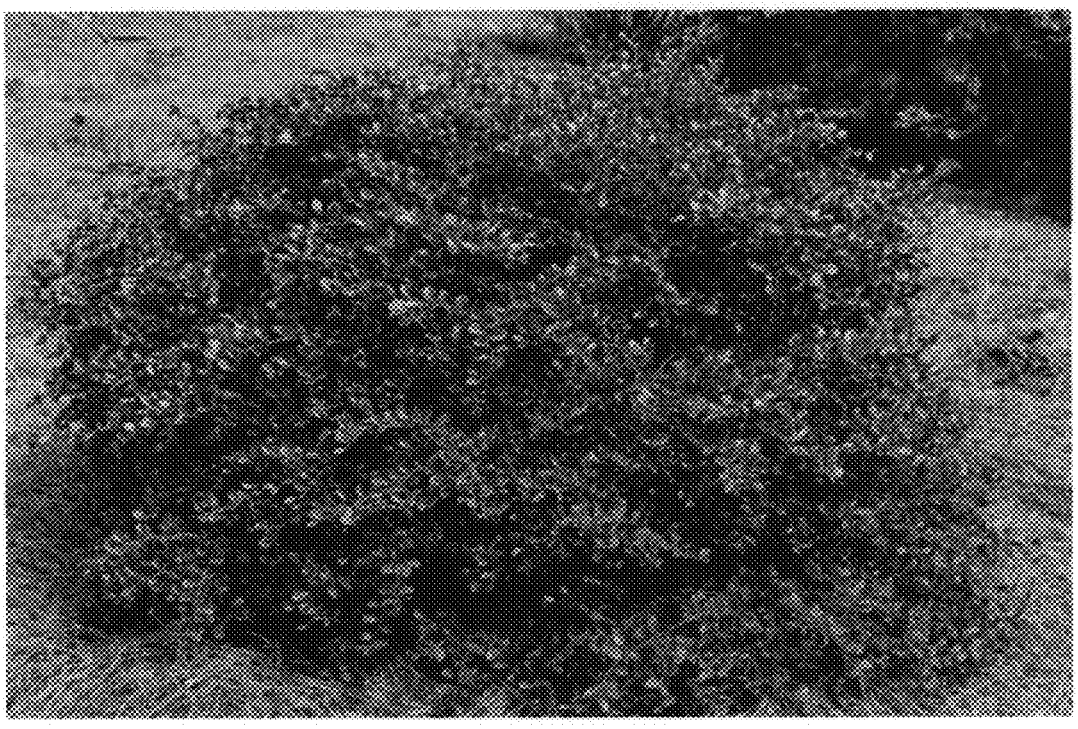
Figure 2:
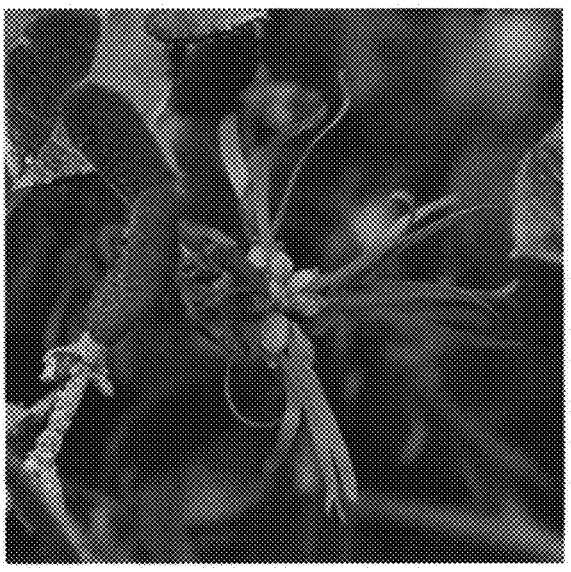

The photograph in FIG. 2 provides a close-up view of a flower of 'PIIIP-I'.

Figure 3:
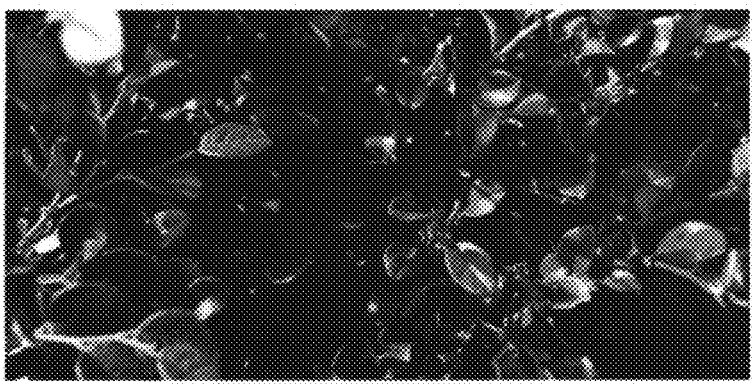

The photograph in FIG. 3 provides a close-up view of the spring and early summer foliage of 'PIIIP-I'.

Figure 4:
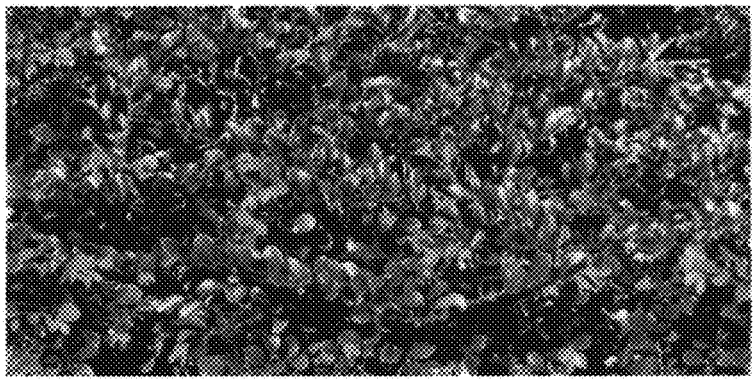

The photograph in FIG. 4 provides a view of the foliage color as it turns color in summer of 'PIIIP-I'.

The colors in the photographs are as close as possible with the photographic and printing technology utilized and the color values cited in the Detailed Botanical Description accurately describe the colors of the new *Lorepetalum.*

DETAILED BOTANICAL DESCRIPTION OF THE PLANT

The following is a detailed description of four year-old plants of the new cultivar as grown in the ground in sun in Watkinsville, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Plant description:

*Blooming period*.—Flowers are produced in April in Watkinsville, Ga. and then sporadically until frost.

*Plant type*.—Evergreen shrub.

*Plant habit*.—Mounded, compact, spreading.

*Height and spread*.—Reaches an average of 92 cm in height and 148 cm in spread for a 4 year-old plant in the landscape.

*Diseases resistance*.—No susceptibility or resistance to diseases or pests has been observed.

*Hardiness*.—At least in U.S.D.A. Zones 7 to 9, good cold hardiness for a purple-leaved cultivar.

*Branching habit*.—Freely branching, pruning enhances lateral branch development.

*Root description*.—Numerous, fine, fibrous and well-branched, 59B in color.

*Propagation*.—Semi-hardwood cuttings.

*Growth rate*.—Moderate.

*Time required for root development*.—An average of six weeks for root initiation (at 32° C.) with a young plant produced in an average of 3 months (at 32° C.).

Branch description:

*Branch shape*.—Rounded.

*Branch size*.—First year; 16 cm in length and 2 mm in diameter, second year and older; 30 cm in length and 5 mm in diameter, trunk; 7 cm in diameter at soil line.

*Branch surface*.—First year; heavily stellate, second year stems; glabrous, trunk; rugose bark.

*Branch color*.—First year; 59A, second year stems; 201B, trunk; 201B.

*Branch strength*.—First year; flexible, older; more easily broken, not as flexible.

*Internode length*.—First year stems; 1.5 cm in length, 2 cm in length.

*Vegetative bud description*.—Alternate in arrangement, surface covered with stellate pubescence, ovoid in shape, 1 mm in length and width, 61A in color.

*Branching*.—Freely branched with pruning enhancing lateral branch development.

Foliage description:

*Leaf division*.—Simple.

*Leaf arrangement*.—Alternate.

*Leaf shape*.—Ovate-rounded.

*Leaf size*.—Average of 2 cm in length and 1.5 cm in width.

*Leaf apex*.—Acute.

*Leaf base*.—Oblique.

*Leaf surface*.—Both surfaces are stellate and rough.

*Leaf margin*.—Entire with stellate hairs.

*Leaf color*.—New growth upper surface; N77A, mature growth upper surface; N137A, new growth lower surface; N77C, mature growth lower surface; 146B.

*Leaf venation*.—Pinnate; color developing upper and lower surfaces; 60A, fully expanded; upper surface 187A, lower surface; 60A.

*Petioles*.—An average of 3.5 mm in length, 1 mm in diameter, 187A in color, stellate pubescent surface.

Inflorescence description:

*Inflorescence type*.—Umbel produced from leaf axils and terminally.

*Lastingness of inflorescence*.—Showy for an average of 2 weeks, individual flowers last 2 to 3 days and are self cleaning.

*Number of flowers*.—4 to 8 flowers per inflorescence.

*Flower form*.—4 to 5 strap-like petals forming a loose funnel.

*Flower buds*.—Obicular in shape, average of 4 mm in length and 3 mm in diameter, N186D in color. pubescent surface.

*Flower fragrance*.—None.

*Flower aspect*.—Outward.

*Petals*.—4, average of 1.6 cm in length and 1 mm in width, linear in shape, acuminate apex, entire margin, truncate base, upper and lower surface smooth, upper surface color; 60B, lower surface color; 63B.

*Sepals*.—4, average of 3.2 mm in length and 2 mm in width, ovate in shape, entire margins, apex is acute to obtuse and reflexed, base is fused into calyx cup, stellate pubescent outer surfaces, glabrous color upper surface 60B, color lower surface is 61B.

*Calyx*.—Average of 3 mm in length, 2 mm in diameter, outer surface N186D in color, inner surface 63A in color, outer surface covered with stellate pubescence, inner surface glabrous.

*Peduncles*.—Average of 6 mm in length and 1 mm in diameter, 63A in color, covered with stellate pubescence.

*Pedicel*.—None, sessile to peduncle.

Reproductive organs:

*Pistil*.—1 to 2, inferior, smooth surface, 2 mm in length, 71B in color, style; 1 mm in length, 71B in color, stigma; rounded, 71B in color, ovary; 1 mm in diameter and length, N81A in color.

*Stamens*.—4 to 5, 1.5 mm in length, 0.3 mm in width, N77 in color, pollen sparse in quantity and 158B in color.

*Fruit*.—2-valved capsule, woody surface, ovoid in shape, an average of 6 mm in length and 4 mm in diameter, 200C in color, 2 seeds per capsule; 5 mm in length, 2 mm in width, 200A in color.

It is claimed:

1. A new and distinct cultivar of *Loropetalum* named 'PIILC-IV' as herein illustrated and described.

* * * * *